(12) United States Patent
Hendershot, III

(10) Patent No.: US 11,234,734 B2
(45) Date of Patent: Feb. 1, 2022

(54) OBTURATOR HAVING AN INSUFFLATION PATHWAY AND AN INSTRUMENT GUIDE

(71) Applicant: Covidien LP, Mansfield, MA (US)

(72) Inventor: John D. Hendershot, III, Madison, CT (US)

(73) Assignee: Covidien LP, Mansfield, MA (US)

( * ) Notice: Subject to any disclaimer, the term of this patent is extended or adjusted under 35 U.S.C. 154(b) by 783 days.

(21) Appl. No.: 16/152,480

(22) Filed: Oct. 5, 2018

(65) Prior Publication Data

US 2019/0038313 A1    Feb. 7, 2019

Related U.S. Application Data

(63) Continuation of application No. 14/736,918, filed on Jun. 11, 2015, now Pat. No. 10,105,161.

(60) Provisional application No. 62/037,719, filed on Aug. 15, 2014.

(51) Int. Cl.
*A61B 17/34* (2006.01)
*A61M 13/00* (2006.01)

(52) U.S. Cl.
CPC ...... *A61B 17/3474* (2013.01); *A61B 17/3417* (2013.01); *A61B 17/3421* (2013.01); *A61M 13/003* (2013.01); *A61B 17/3423* (2013.01); *A61B 2017/3445* (2013.01); *A61B 2017/3456* (2013.01); *A61B 2017/3482* (2013.01)

(58) Field of Classification Search
CPC ............ A61B 17/3474; A61B 17/3417; A61B 17/3421; A61B 17/3423; A61B 2017/3445; A61B 2017/3456; A61B 2017/3482; A61M 13/003
See application file for complete search history.

(56) References Cited

U.S. PATENT DOCUMENTS

| 5,637,075 A | 6/1997 | Kikawada |
| 5,716,369 A * | 2/1998 | Riza ................... A61B 17/0469 606/139 |
| 5,944,654 A | 8/1999 | Crawford |
| 6,283,948 B1 * | 9/2001 | McKernan ......... A61B 17/3417 604/272 |

(Continued)

*Primary Examiner* — Rebecca E Eisenberg
*Assistant Examiner* — John A Doubrava
(74) *Attorney, Agent, or Firm* — Carter, DeLuca & Farrell LLP

(57) ABSTRACT

A surgical access apparatus is presented including a cannula having a housing and a cannula shaft, the cannula shaft defining an internal lumen and a slot in communication with the internal lumen and an obturator insertable through the internal lumen of the cannula. The obturator includes an obturator shaft having a proximal end and a distal end and a tip member disposed at the distal end of the obturator shaft, the tip member configured to form an incision through tissue. An outer surface of the obturator shaft and the tip member defines a channel for receiving and directing insufflation fluid into a body cavity, a portion of the same channel also configured to guide a surgical instrument, such as a suture passer/grasper for closing an incision, towards and through the slot. In this way, the cannula and obturator can be employed both for forming an incision at the beginning of a surgical procedure and for closing the same incision at the conclusion of the surgical procedure.

17 Claims, 9 Drawing Sheets

(56) References Cited

U.S. PATENT DOCUMENTS

| | | | |
|---|---|---|---|
| 7,150,713 B2 * | 12/2006 | Shener | A61B 1/00071 |
| | | | 600/156 |
| 7,182,752 B2 * | 2/2007 | Stubbs | A61B 17/3421 |
| | | | 604/164.01 |
| 7,708,713 B2 | 5/2010 | Albrecht et al. | |
| 8,109,943 B2 * | 2/2012 | Boraiah | A61B 17/34 |
| | | | 606/139 |
| 8,123,676 B2 | 2/2012 | Kucklick | |
| 8,202,290 B2 | 6/2012 | Smith | |
| 8,353,874 B2 * | 1/2013 | Okoniewski | A61B 17/3474 |
| | | | 604/167.03 |
| 8,574,238 B2 | 11/2013 | Zannis et al. | |
| 9,265,899 B2 * | 2/2016 | Albrecht | A61M 13/003 |
| 10,105,161 B2 | 10/2018 | Hendershot, III | |
| 2004/0204671 A1 | 10/2004 | Stubbs | |
| 2006/0095054 A1 * | 5/2006 | Zannis | A61B 17/0401 |
| | | | 606/148 |
| 2006/0167475 A1 | 7/2006 | Bischof et al. | |
| 2012/0232339 A1 | 9/2012 | Csiky | |
| 2012/0316593 A1 | 12/2012 | Kim | |
| 2013/0079597 A1 | 3/2013 | Auerbach et al. | |
| 2013/0116510 A1 | 5/2013 | Lutze et al. | |
| 2013/0190570 A1 | 7/2013 | Hirsch et al. | |
| 2013/0245381 A1 | 9/2013 | Dang | |
| 2014/0114360 A1 | 4/2014 | Gephart et al. | |
| 2014/0163323 A1 * | 6/2014 | Mohajer-Shojaee | |
| | | | A61B 17/3498 |
| | | | 600/204 |
| 2015/0038997 A1 * | 2/2015 | Malkowski | A61B 17/0483 |
| | | | 606/148 |
| 2015/0272617 A1 | 10/2015 | MacDonald | |
| 2016/0000462 A1 * | 1/2016 | Pajunk | A61B 17/3421 |
| | | | 604/26 |

* cited by examiner

OBTURATOR HAVING AN INSUFFLATION PATHWAY AND AN INSTRUMENT GUIDE

CROSS-REFERENCE TO RELATED APPLICATIONS

The present application is a continuation of U.S. patent application Ser. No. 14/736,918, filed Jun. 11, 2015, now U.S. Pat. No. 10,105,161 which claims the benefit of and priority to U.S. Provisional Patent Application Ser. No. 62/037,719, filed Aug. 15, 2014, the entire disclosure of which are incorporated by reference herein.

BACKGROUND

Technical Field

The present disclosure relates to a surgical access assembly including an obturator and a cannula. More particularly, the present disclosure relates to an obturator with an outer surface having a channel for transmitting fluids therealong, as well as for guiding surgical instruments through slots on the cannula.

Background of Related Art

Minimally invasive procedures are continually increasing in number and variation. Forming a relatively small diameter, temporary pathway to the target site is a key feature of most minimally invasive surgical procedures. The most common method of providing such a pathway is by inserting an access assembly through the skin. Common access assemblies generally include a cannula configured to accommodate a trocar for penetrating tissue, and an obturator for dilating and creating a pathway through tissue. Obturators may be blunt members that are inserted through the cannula to tunnel a path through tissue and subsequently to a selected surgical site.

Minimally invasive procedures often supply insufflation fluids, e.g., carbon dioxide, to a body cavity underlying a layer of tissue such that the layer of tissue lifts away from underlying tissue or organ structures to create a larger working space. To this end, a source of insufflation fluid may be coupled to the cannula such that insufflation fluids flow distally into a body cavity. In many procedures, it is desirable to insufflate the body cavity of a patient while the obturator is inserted through the cannula. In such an arrangement, insufflation fluids may be introduced through an interior portion of the obturator, and exit through an opening in a distal portion or tip of the obturator within the working space. Such an arrangement typically incorporates an additional source of insufflation fluid coupled with the obturator, as well as a sealing member within the obturator to inhibit the proximal migration of insufflation fluids through the obturator.

SUMMARY

According to one aspect of the present disclosure, a surgical access apparatus is presented. The surgical access apparatus includes a cannula including a housing and a cannula shaft, the cannula shaft defining an internal lumen and at least one slot in communication with the internal lumen and an obturator insertable through the internal lumen of the cannula. The obturator includes an obturator shaft having a proximal end and a distal end and a tip member disposed at the distal end of the obturator shaft, the tip member configured to be inserted through tissue. An outer surface of the obturator shaft and the tip member defines a channel for receiving insufflation fluid.

In one exemplary embodiment, the obturator is configured to receive an endoscope.

In another exemplary embodiment, the channel is not in fluid communication with an interior of the obturator. The channel extends from a proximalmost end of the obturator shaft to a distalmost end of the tip member.

In yet another exemplary embodiment, when the obturator shaft is disposed in the lumen of the cannula shaft, an annular space is defined between the obturator shaft and the cannula shaft. The annular space is configured to receive a surgical instrument therethrough.

In another exemplary embodiment, at least one seal member is disposed in the cannula and is configured to form a fluid-tight seal with the obturator inserted therethrough.

In yet another exemplary embodiment, the at least one slot includes two slots in opposed relation thereof and the cannula is configured to be coupled to a source of fluid. The two slots each include a sealing member configured to be penetrated by a distal end of a surgical instrument.

In another exemplary embodiment, the channel is configured to receive a surgical instrument therethrough, a distal end of the surgical instrument configured to extend through the at least one slot. The channel is further configured to direct the insufflation fluid to the tip member of the obturator.

According to another aspect of the present disclosure, a surgical access assembly is presented. The surgical access assembly includes a cannula assembly including a cannula defining two slots in opposed relation thereof and an obturator assembly including an obturator shaft having a tip member at a distal end thereof, the obturator shaft and tip member having an outer surface that defines a channel, the channel configured to convey insufflation fluid from a proximalmost end of the obturator shaft to a distalmost end of the tip member.

According to another aspect of the present disclosure, a method of accessing a surgical site is presented. The method of accessing a surgical site for performing a surgical procedure includes inserting at least a portion of a cannula assembly through tissue, the cannula assembly including a cannula defining two slots in opposed relation thereof, inserting an obturator assembly through the cannula assembly, the obturator assembly including an obturator shaft having a tip member at a distal end thereof, the obturator shaft and tip member having an outer surface that defines a channel, conveying insufflation fluid, via the channel, from a proximalmost end of the obturator shaft to a distalmost end of the tip member, and, upon completion of the surgical procedure, inserting a surgical instrument through the channel, a distal end of the surgical instrument extending through one of the two slots.

The present invention, according to various embodiments thereof, may also relate to a surgical access apparatus, comprising a cannula including a housing and a cannula shaft, the cannula shaft defining an internal lumen and a slot in communication with the internal lumen; and an obturator insertable through the internal lumen of the cannula, the obturator including: an obturator shaft having a proximal end and a distal end; and a tip member disposed at the distal end of the obturator shaft, the tip member configured to be inserted through tissue; wherein an outer surface of the obturator shaft and the tip member defines a channel for receiving insufflation fluid, the channel also configured to guide a surgical instrument towards and through the slot.

The obturator may be transparent so as to enable visualization when an endoscope is positioned therein. The channel may avoid fluid communication with an interior of the obturator. The channel may extend from a proximalmost end of the obturator shaft to a distalmost end of the tip member. When the obturator shaft is disposed in the lumen of the cannula shaft, an annular space may be defined between the obturator shaft and the cannula shaft. The surgical instrument may be a suture passer/grasper configured to close an incision. At least one seal member may be disposed in the cannula and may be configured to form a fluid-tight seal with the obturator inserted therethrough.

The at least one slot may include two slots in opposed relation thereof. The two slots may each include a sealing member configured to be penetrated by a distal end of a surgical instrument. The cannula may be configured to be coupled to a source of fluid. The channel may be configured to receive a surgical instrument therethrough, a distal end of the surgical instrument configured to extend through the at least one slot. The channel may be configured to direct the insufflation fluid to the tip member of the obturator.

In accordance with various embodiments, the present invention may also relate to a surgical assembly comprising: a cannula assembly for providing access through a surgical incision, the cannula assembly including a cannula shaft defining a slot therethrough; and an obturator assembly including an obturator shaft having a tip member at a distal end thereof, the obturator shaft and tip member having an outer surface that defines a channel, the channel configured to convey insufflation fluid from a proximalmost end of the obturator shaft to a distalmost end of the tip member, the channel further configured to direct a surgical instrument through the slot so as to enable the surgical incision to be sutured closed at the conclusion of the surgical procedure.

The channel may avoid being in fluid communication with an interior of the obturator. When the obturator shaft is disposed in a lumen of the cannula, an annular space may be defined between the obturator shaft and the cannula. The cannula may define two opposing slots. The slot may include a sealing member configured to be penetrated by a distal end of the surgical instrument. In an embodiment, at least one seal member is disposed in the cannula assembly and is configured to form a fluid-tight seal with the obturator assembly inserted therethrough.

In still other embodiments of the present invention, there is provided a method of performing a surgical procedure, the method comprising: inserting an obturator assembly into a cannula assembly, the cannula assembly including a cannula shaft defining a slot therethrough, the obturator assembly including an obturator shaft having a tip member at a distal end thereof, the obturator shaft and tip member having outer surfaces that define a channel; moving the combined obturator assembly and cannula assembly such that the tip member of the obturator shaft forms an incision through tissue; conveying insufflation fluid, along the outer surfaces of the obturator shaft and the tip member via the channel and into a body cavity; removing the obturator from the cannula; upon completion of the surgical procedure, reinserting the obturator into the cannula; and inserting a surgical instrument such that the channel guides a distal end of the surgical instrument through the slot.

The method may further comprise the steps of: prior to the moving step, inserting an endoscope into the obturator assembly; and using the endoscope to visualize the incision being formed by the tip member. The surgical instrument may be a suture passer/grasper configured to close the incision.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Figure 1:
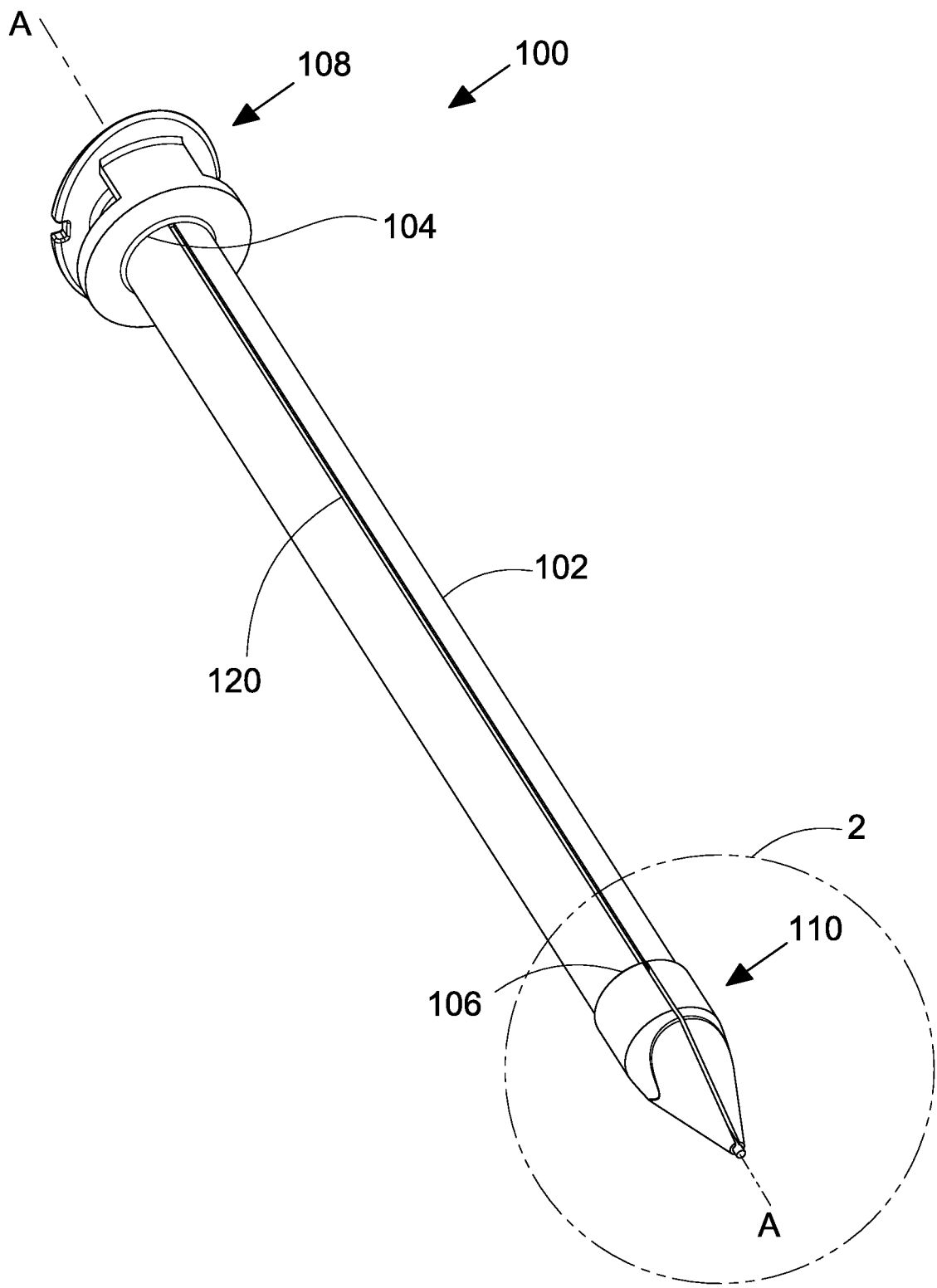
FIG. 1 is a perspective view of an obturator including a tip member in accordance with the present disclosure.

Embodiments of the presently disclosed surgical access apparatus for use in minimally invasive procedures are described in detail with reference to the drawings, in which like reference numerals designate identical or corresponding elements in each of the several views. As used herein, the term "distal" refers to that portion of the apparatus which is farther from the operator while the term "proximal" refers to that portion of the apparatus which is closer to the operator. The presently disclosed surgical access apparatus is usable in an opening through a patient's tissue, such as an incision or a naturally-occurring orifice (e.g., mouth, anus, or vagina).

Figure 4:
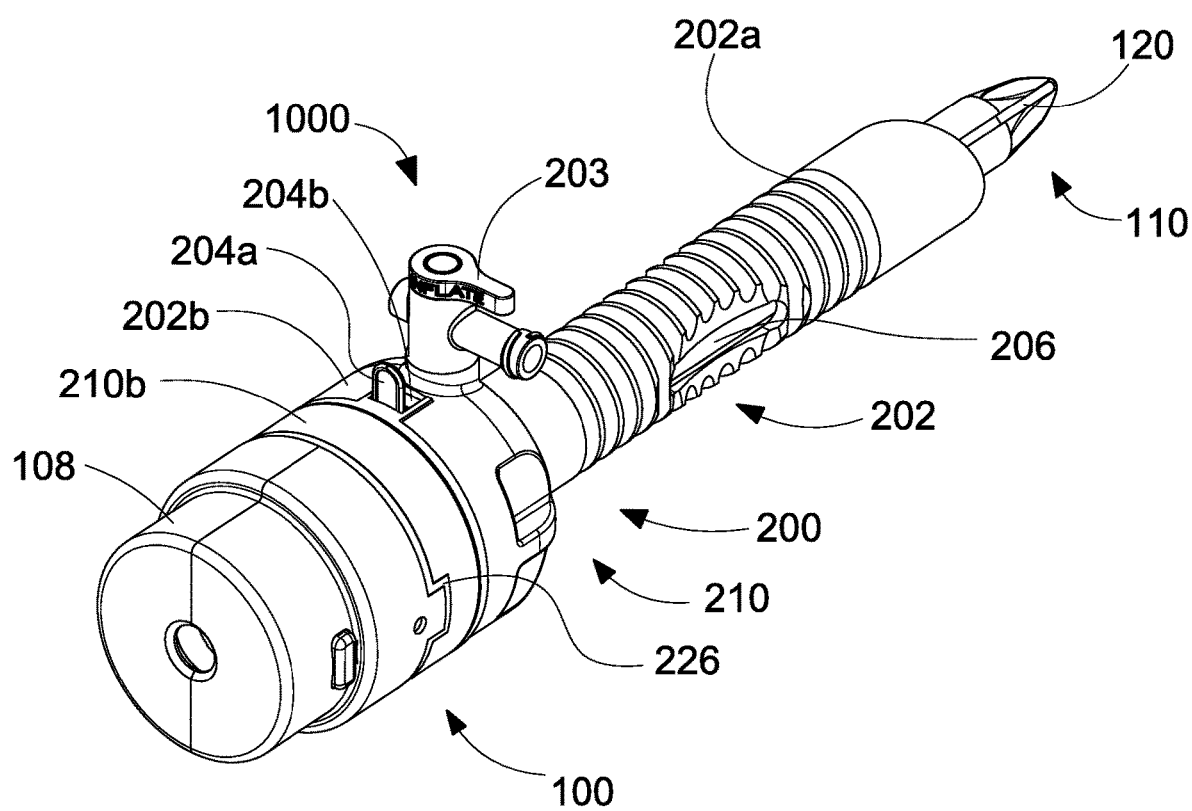
FIG. 4 is a perspective view of a surgical access apparatus according to the present disclosure, including the obturator of FIG. 1.

Referring initially to FIG. 4, a surgical access apparatus 1000 is shown. Surgical access apparatus 1000 includes an obturator 100 insertable through a cannula 200, which will be described further in detail below.

Referring now to FIG. 1, obturator 100 includes an obturator shaft 102, a tip member 110, and a handle 108. Obturator shaft 102 is an elongate member that defines a longitudinal axis "A," and has a proximal end 104 and a distal end 106. The handle 108 is mounted to the proximal end 104 of obturator shaft 102 and may include surface features suitable for grasping by an operator, e.g., an ergonomic grip incorporating flanges, curves, knurls, or the like. A channel 120 is formed on an outer surface of the obturator shaft 102. The channel 120 extends from the proximalmost end 104 of the obturator shaft 102 to the distalmost end 112 of the tip member 110, as described below. Channel 120 may be a single, continuous, non-interrupted channel that extends the length of the obturator 100.

Figure 2:
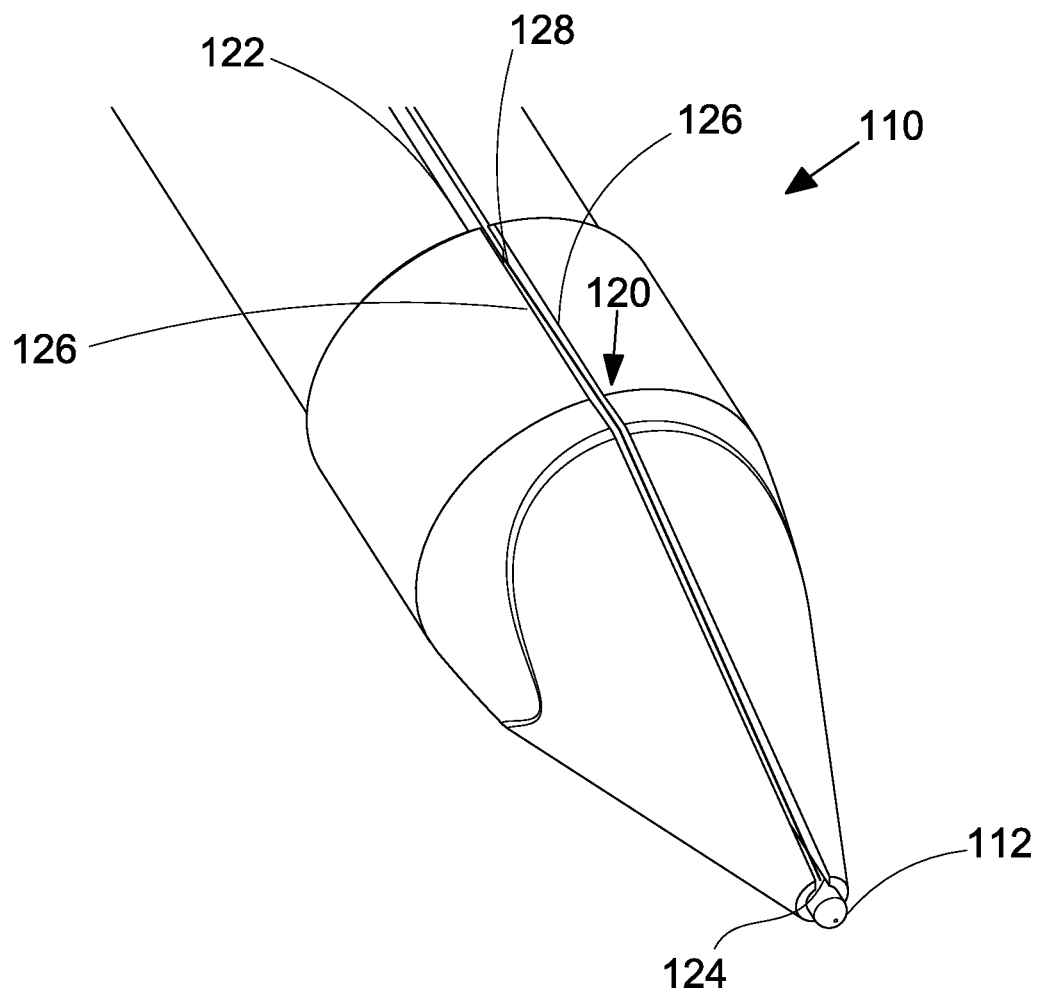
FIG. 2 is an enlarged view of the area of detail identified in FIG. 1.

Turning to FIG. 2, the tip member 110, as shown, may have a tapered, e.g., conical, pyramidal, curved, etc., configuration that tapers to a distal tip 112. Distal tip 112 may be blunt, as shown, or may have another desirable atraumatic configuration, e.g., curvate, spheroid, or flat. In other embodiments, distal tip 112 may be sharpened or pointed so as to be configured to penetrate tissue.

The channel 120 is formed on an outer surface of the obturator shaft 102, as well as on the outer surface of the tip member 110. Channel 120, as shown, is contoured to the outer surface of tip member 110 and extends along the length of tip member 110, as well as the length of the obturator shaft 102. Channel 120 includes an open proximal end 122 opposite an open distal end 124. Distal end 124 may be coterminous with distal tip 112, or distal tip 112 may protrude past the distal end 124 of channel 120, as shown. Channel 120 is defined by a pair of opposed walls 126 joined by a channel floor 128. Channel 120 may have any desirable configuration, e.g., arcuate or U-shaped, or may be configured as a closed member extending along the tip member 110, e.g., a tube or box when viewed in cross-section. Channel 120 defines a path through which fluids, e.g., insufflation fluids, may flow. Additionally, channel 120 defines a path through which surgical instruments are directed or guided through. In further embodiments, the walls 126 or channel floor 128 may incorporate surface features such as grooves or curves, e.g., to direct or alter fluid flow through channel 120.

In some instances, the outer diameter of the obturator 100 may closely match the inner diameter of cannula 200 (see FIG. 4). Thus, channel 120 extends along the entire length of obturator 100 or substantially the entire length of obturator 100. The channel 120 may be fluidly coupled directly to insufflation port 214 (see FIGS. 7-10).

Channel 120 is formed on an outer surface of tip member 110 and the obturator shaft 102 by, e.g., cutting, etching, laser treatment, electrical arcing, and the like. In some embodiments, tip member 110, as well as obturator shaft 102 may be molded in a die or template such that channel 120 is pre-formed thereon. Those skilled in the art may envision other suitable methods of forming channel 120 across the length of the obturator 100.

Figure 3:
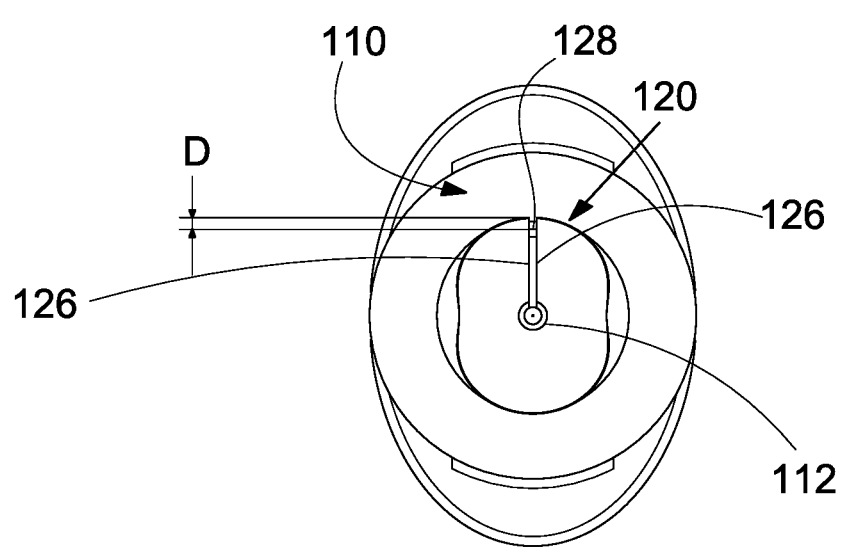
FIG. 3 is a bottom plan view of the obturator shown in FIG. 1.

Referring to FIG. 3, channel 120, as shown, extends radially inward at a depth "D" along the outer surface of the tip member 110. Depth D, as shown, may be a constant dimension measured radially inward from an outer surface of the tip member 110. In this manner, channel floor 128 is disposed a depth D from the outer surface of tip member 110 as the channel 120 extends along the outer surface of the obturator shaft 102 toward the tapered profile of the tip member 110 and toward the distal tip 112. In embodiments, the depth D of channel 120 may vary along the longitudinal length of the obturator shaft 102 and the tip member 110, e.g., the distance between the outer surface of the tip member 110 and the channel floor 128 may increase or decrease along the longitudinal length of obturator shaft 102 and the tip member 110.

Referring back to FIG. 1, tip member 110 is shown coupled with obturator shaft 102. Tip member 110 may be mounted to the distal end 106 of obturator shaft 102 by any suitable means, e.g., press-fit, threaded connection, bayonet-type coupling, adhesion, or ultrasonic welding. In embodiments, tip member 110 and obturator shaft 102 may be integrally formed. Referring back to FIGS. 2 and 3, the open proximal end 122 of channel 120 provides an entrance path to channel 120 as a fluid, e.g., insufflation fluid, advances distally along the obturator shaft 102 toward the tip member 110. Tip member 110, as shown, may have a hollow interior, or may be a solid member. Advantageously, tip member 110 and shaft 102 may be transparent, such that an endoscope positioned therein allows visualization of the tissue during penetration.

Figure 5:
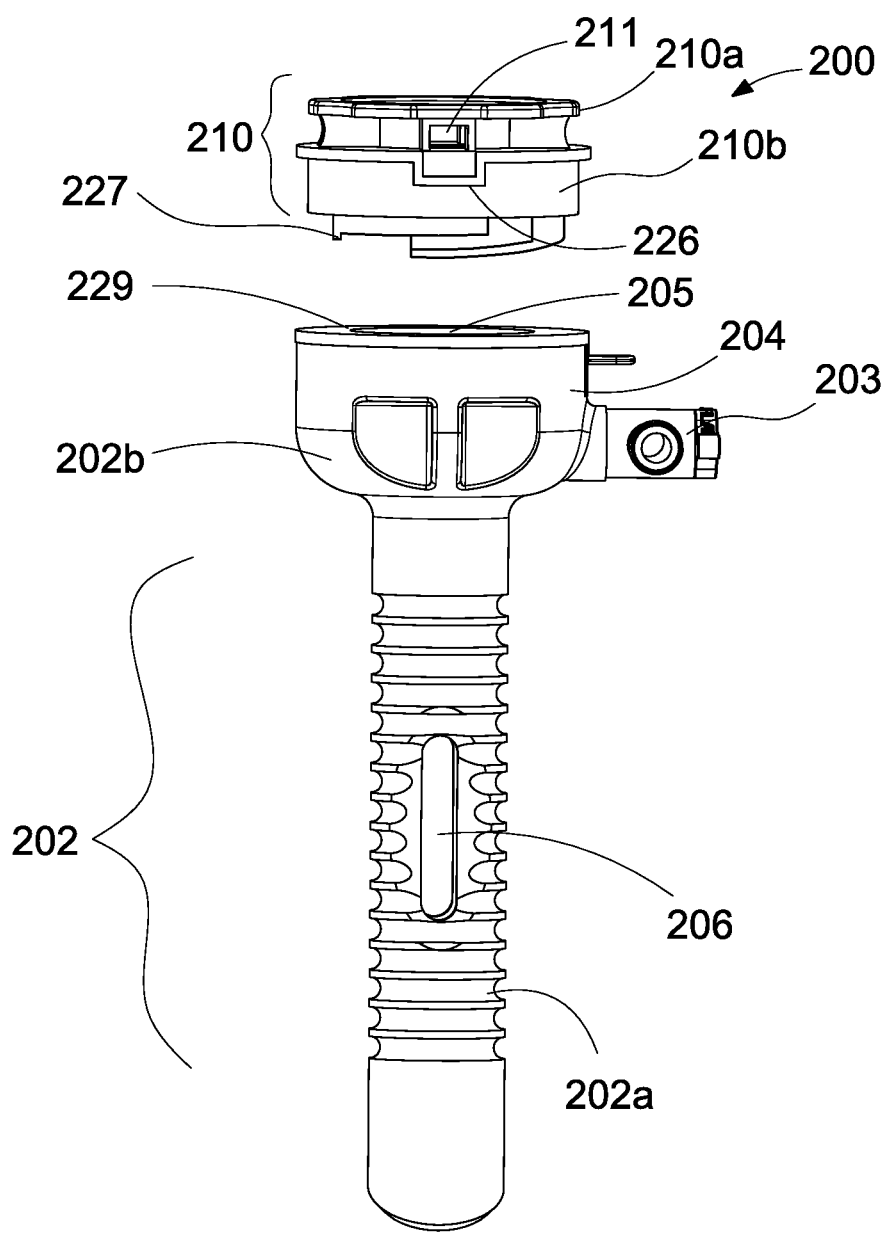
FIG. 5 is a perspective view of the cannula of FIG. 4 with the housing and elongated portion of the cannula shown separated from each other.

Referring to FIGS. 1 and 4-6B, cannula 200 of surgical access assembly 1000 includes an elongated portion 202 and a housing 210 including a proximal housing component 210a and a distal housing component 210b (see FIG. 5). Elongated portion 202 includes elongated tubular member 202a and a base member 202b. Base member 202b includes threading 229 configured to engage complementary threading 227 of distal housing component 210b (see FIG. 5), e.g., via a bayonet connection, to releasably engage housing 210 and elongated portion 202 to each other. Base member 202b further includes an insufflation port 203 allowing for the selective inflow and outflow of insufflation fluid. A collar 204 is configured to be seated within base member 202b. Collar 204 further includes a tab 204a disposed within a recess 204b defined within base member 202b and selectively movable within recess 204b to unlock housing 210 from base member 202b, thus permitting disengagement of housing 210 from base member 202b. Elongated tubular member 202a extends distally from base member 202b and may be formed from a translucent material, although other configurations are also contemplated.

Proximal end distal housing components 210a, 210b, respectively, of housing 210 may be selectively engageable with each other via snap-fit engagement or other suitable arrangement to form housing 210. Alternatively, these components may be integrally formed with each other, e.g., welded, snap-fit, etc.

Proximal housing component 210a defines a pair of radially opposed apertures 211 (see FIG. 5) extending therethrough. Distal housing component 210b includes a pair of notches 226 configured to mechanically engage a pair of corresponding latches associated with obturator handle 108 (see FIG. 1) to selectively lock and unlock obturator 100 to and from cannula 200. More specifically, obturator handle 108 is configured to receive proximal housing component 210a therein as elongated obturator shaft 102 is inserted into elongated tubular member 202a, ultimately such that latches of obturator 100 are received within apertures 211 of proximal housing component 210a to selectively lock obturator 100 and cannula 200 with each other. As noted above, housing 210 and elongated portion 202 are releasably engageable with each other, e.g., via engagement of threadings 227, 229, respectively.

Figures 6A, 6B:
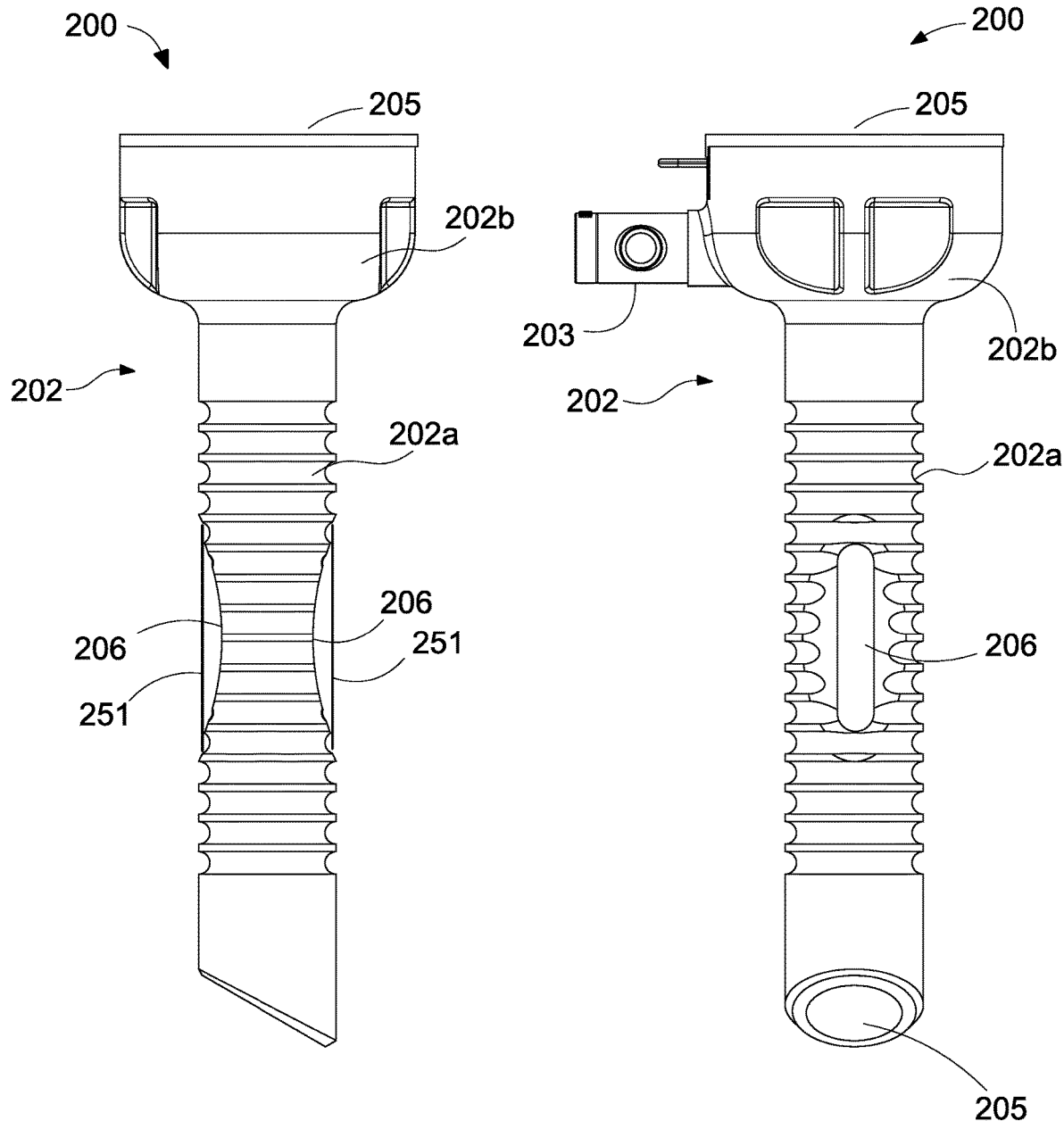
FIG. 6A is a first side view of the cannula of FIG. 4A with the housing removed.
FIG. 6B is a second side view rotated 90 degrees of the cannula of FIG. 4A with the housing removed.
Figure 7:
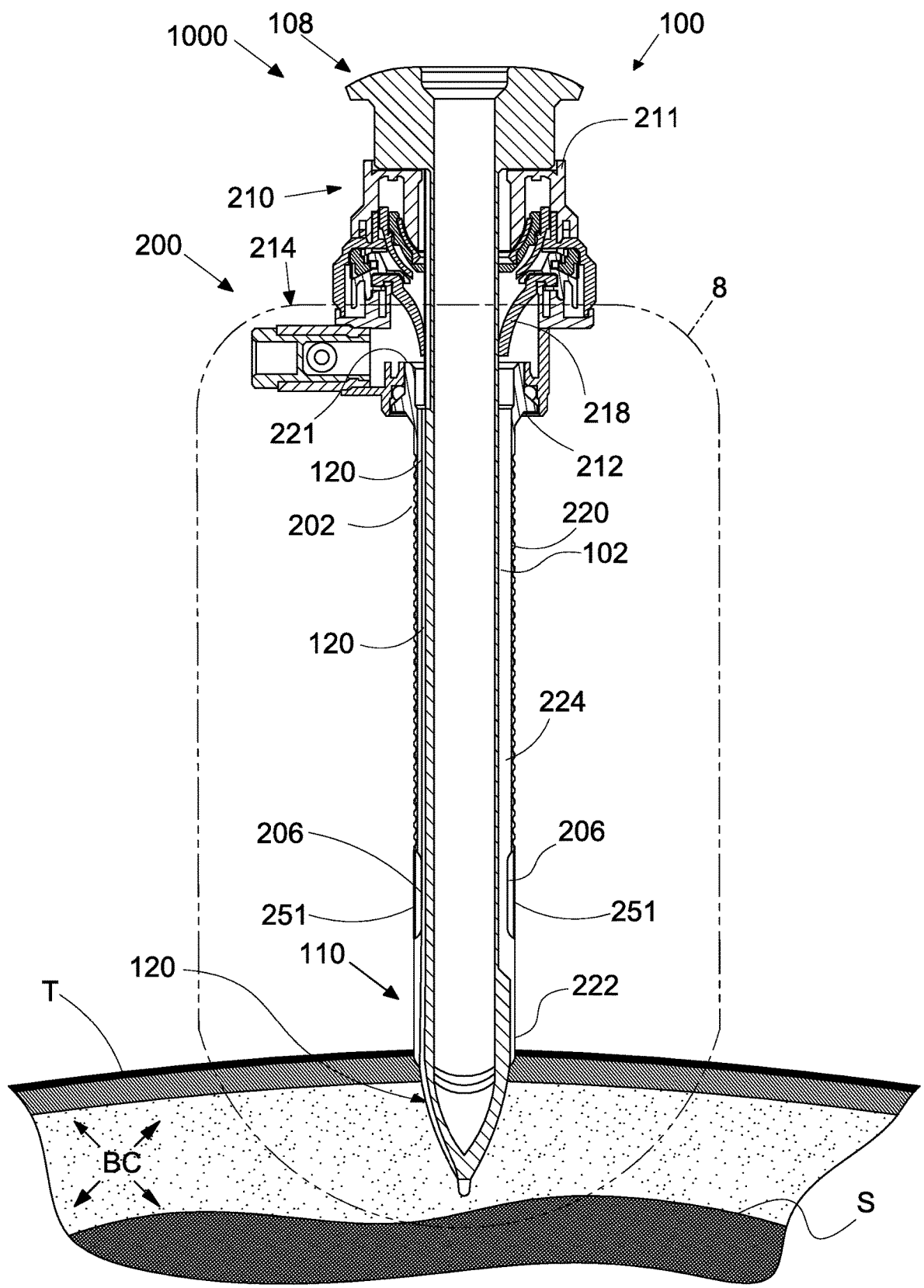
FIG. 7 is a cross-sectional view of FIG. 4, shown together with a cross-section of a layer of tissue and underlying body cavity.
Figure 8:
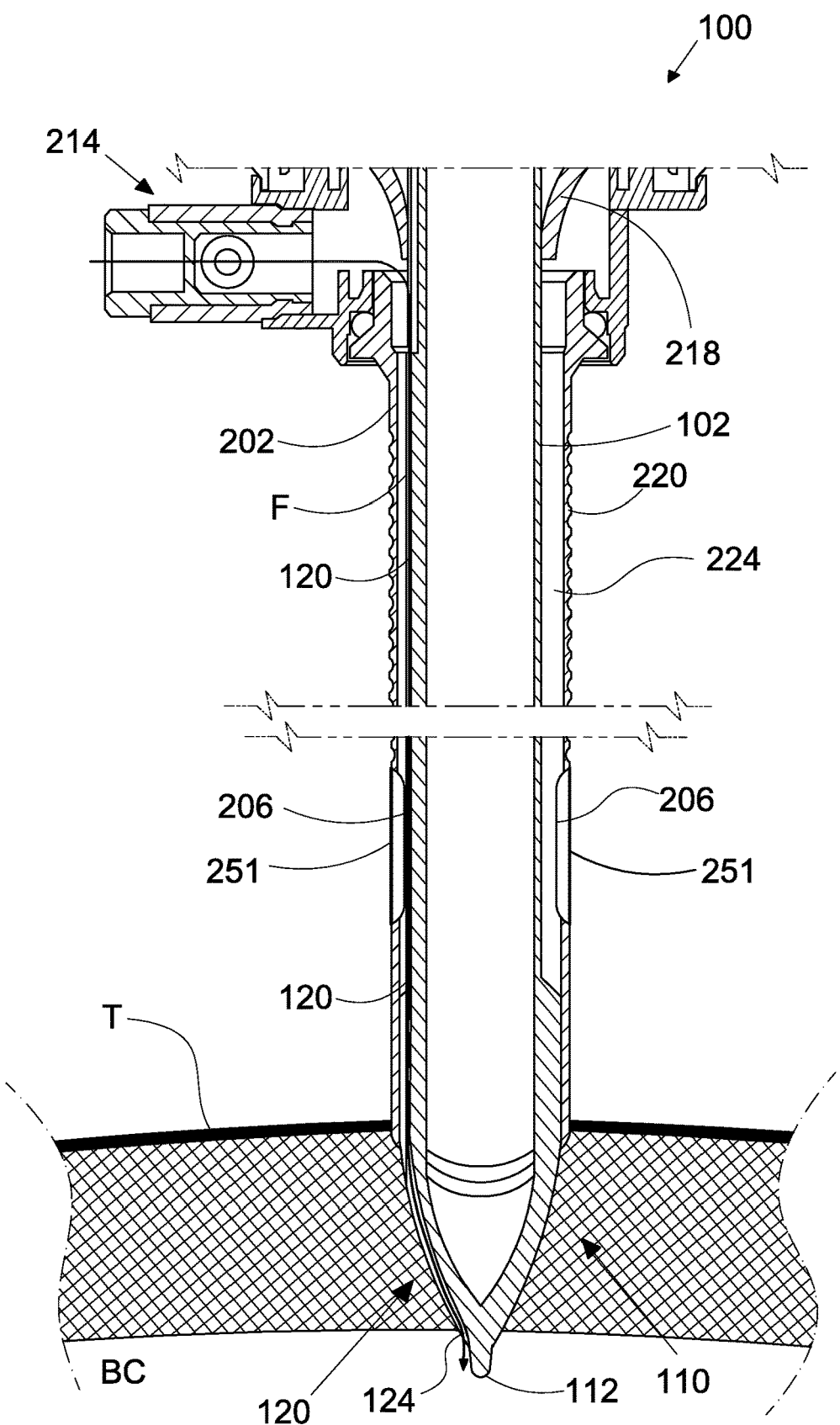
FIG. 8 is an enlarged view of the area of detail identified in FIG. 7.

With reference in particular to FIGS. 5-6B, elongated tubular member 202a of cannula 200 may be provided in various different configurations, e.g., various diameters between about 5 mm to about 15 mm and/or various lengths from about 70 mm to about 150 mm, although other suitable configurations are also contemplated. Elongated tubular member 202a may define a ribbed exterior (as shown) or may define a generally smooth exterior, depending on a particular purpose. Elongated tubular member 202a is configured for positioning within an opening in tissue and defines a longitudinal passageway 205 extending therethrough that is configured to receive surgical instrumentation (not shown) for guiding the surgical instrumentation through the opening in tissue and into the internal surgical site. Passageway 205 of elongated tubular member 202a is further configured to receive elongated obturator shaft 102 of obturator 100 (see FIG. 1) to facilitate insertion of elongated tubular member 202a into the opening in tissue.

A pair of opposed slots 206 extend through the annular side wall of elongated tubular member 202a (see FIG. 6A), thus providing lateral access to and from longitudinal passageway 205 to and from the exterior of elongated tubular member 202a. Opposed slots 206 may be positioned along the length of elongated tubular member 202a at any suitable position, e.g., closer to or further from base member 202b of elongated portion 202 of cannula 200.

Thus, a cannula 200 including a particular positioning of slots 206 may be selected based upon on the procedure being performed, the location of the opening in tissue, the patient's anatomy, the user's preference, and/or other factors. For some procedures, it has been found to be desirable that, once cannula 200 is positioned within the opening in tissue, slots 206 are positioned distally of the skin and fatty layers of tissue and adjacent to the fascia and muscle layers of tissue since fascia and muscle layers are better suited to receive and retain a suture for closing the opening in tissue. Thus, a cannula 200 having slots 206 positioned to achieve this configuration may be selected. However, other configurations are also contemplated. Further, as an alternative or in addition to providing multiple cannulas 200 having differently positioned slots 206, multiple pairs of opposed slots 206 may be spaced-apart along the length of elongated tubular member 202a such that an appropriately positioned pair of slots 206 may be utilized, e.g., depending on the procedure being performed, the location of the opening in tissue, the patient's anatomy, the user's preference, and/or other factors.

Turning now to FIGS. 7-10, the obturator 100 is configured for insertion through cannula 200. Cannula 200 includes a housing 210 and a cannula shaft 220 extending distally from the housing 210. Housing 210 defines an interior annular recess and includes a proximal end 211 and a distal end 212 each defining an aperture configured to accommodate insertion of the obturator shaft 102 therethrough. Cannula shaft 220 has an open proximal end 221 opposite an open distal end 222, and defines an internal lumen 224 extending from the proximal end 221 to the distal end 222. Lumen 224 is dimensioned to accommodate passage of the obturator shaft 102 and tip member 110 through the cannula shaft 220.

A seal member 218, as shown, may be disposed within housing 210. Seal member 218 may be press fit, adhered, welded, or otherwise secured within housing 210. Seal member 218 is configured to sealably engage obturator shaft 102, or an instrument inserted therethrough. Accordingly, seal member 218 may be configured as a septum, conical, or disc seal. In embodiments, seal member 218 may be configured as a zero-closure seal, e.g., a duckbill, and may be configured to inhibit the proximal migration of fluids through cannula 200 in the absence of an instrument inserted therethrough. In further embodiments, cannula 200 may incorporate multiple seal members of varying configurations. Such seal members may be disposed in either or both the cannula housing 210 or cannula shaft 220.

Obturator 100, as shown, is insertable through lumen 224 of cannula shaft 220. Obturator 100 is dimensioned such that upon engagement of the handle 108 with the proximal end 211 of housing 210 of cannula 200, channel 120 is exposed across the length of the cannula shaft 220. At least a portion of tip member 110 remains disposed within lumen 224.

Housing 210, as shown, includes an insufflation port 214 for transmitting fluids, e.g., insufflation fluids, therethrough. Insufflation port 214 may be configured as a stopcock or other suitable fluid port. Insufflation port 214 may be coupled with, e.g., a source of insufflation fluid or vacuum, or to a fluid line connected to a fluid source. Insufflation port 214 may include a valve or fluid lock for selectively controlling the flow of fluids through insufflation port 214.

With continued reference to FIGS. 7-10, the surgical access apparatus 1000, as shown, is configured to be inserted through a layer of tissue "T." Tissue T defines a body cavity "BC," which may include underlying structures "S," such as tissue or body organs. FIGS. 7-10 further illustrate a penetration or incision of tissue T. An operator may grasp handle 108 of obturator 100 and, upon distal movement of obturator 100, tip member 110 dilates and advances through tissue T, creating a path for cannula shaft 220 to be inserted through tissue T.

Cannula shaft 220 includes the pair of opposed slots 206. The pair of opposed slots 206 are selectively positionable relative to the tissue T by a user inserting or withdrawing the cannula shaft 220 to a desired depth, as will be described more fully below. As mentioned previously, cannula shaft 220 may be transparent such that the position of cannula 200 within the tissue may be viewed by a user with an endoscope positioned within the cannula shaft 220. For instance, an endoscope so positioned may inform a user as to when the distal end 222 is within the incision or when the slots 206 are at a depth relative to the tissue T such that sutures/graspers inserted through the slots 206 will penetrate the tissue T at a desired depth for closing the fascial layers of the tissue after a surgery has been completed. Additionally, the user could know when the surgical access apparatus 1000 is in a position where insufflation fluid would be effectively trapped by the tissue and retained within the insufflation channel 120. Insufflation fluids "F" are introduced through insufflation port 214 and into lumen 224 of cannula shaft 220 and into channel 120, which extends the length of the obturator shaft 102. The presence of the obturator shaft 102 having the channel 120 within lumen 224 defines an annular space through which insufflation fluids F flow (see FIG. 8).

Seal member 218, as described above, inhibits the proximal migration of insufflation fluids F through the cannula shaft 220. Accordingly, pressurized insufflation fluids F entering cannula 200 through insufflation port 214 advance distally through lumen 224 and the channel 120 toward tip member 110.

Channel 120 is exposed within the lumen 224 such that insufflation fluids F may enter channel 120 and advance distally into body cavity BC. Channel 120 extends the length of the obturator shaft 102. The proximalmost end of channel 120 is located adjacent the insufflation port 214, whereas the distalmost end of the channel 120 is located at or near the tip 112 of the tip member 110. As pressurized fluids build up within lumen 224, channel 120 provides a path of least resistance along which pressurized insufflation fluids F will escape the higher-pressure environment within lumen 224. Accordingly, controlling the rate of flow through insufflation port 214 affects the fluid pressure within lumen 224 and the flow of insufflation fluids F along channel 120 and into body cavity BC.

In this manner, the supply of insufflation fluids F to body cavity BC is achieved directly through the cannula 200 between the inner wall of the cannula shaft 202 and the outer wall of the obturator shaft 102. The passage of insufflation fluids F along an outer surface of the obturator shaft 102 and the tip member 110 of obturator 100 obviates the need for insufflation gas to enter into the interior of the obturator shaft 102 and the need for accompanying sealing structures which such prior art arrangements require.

Figure 9:
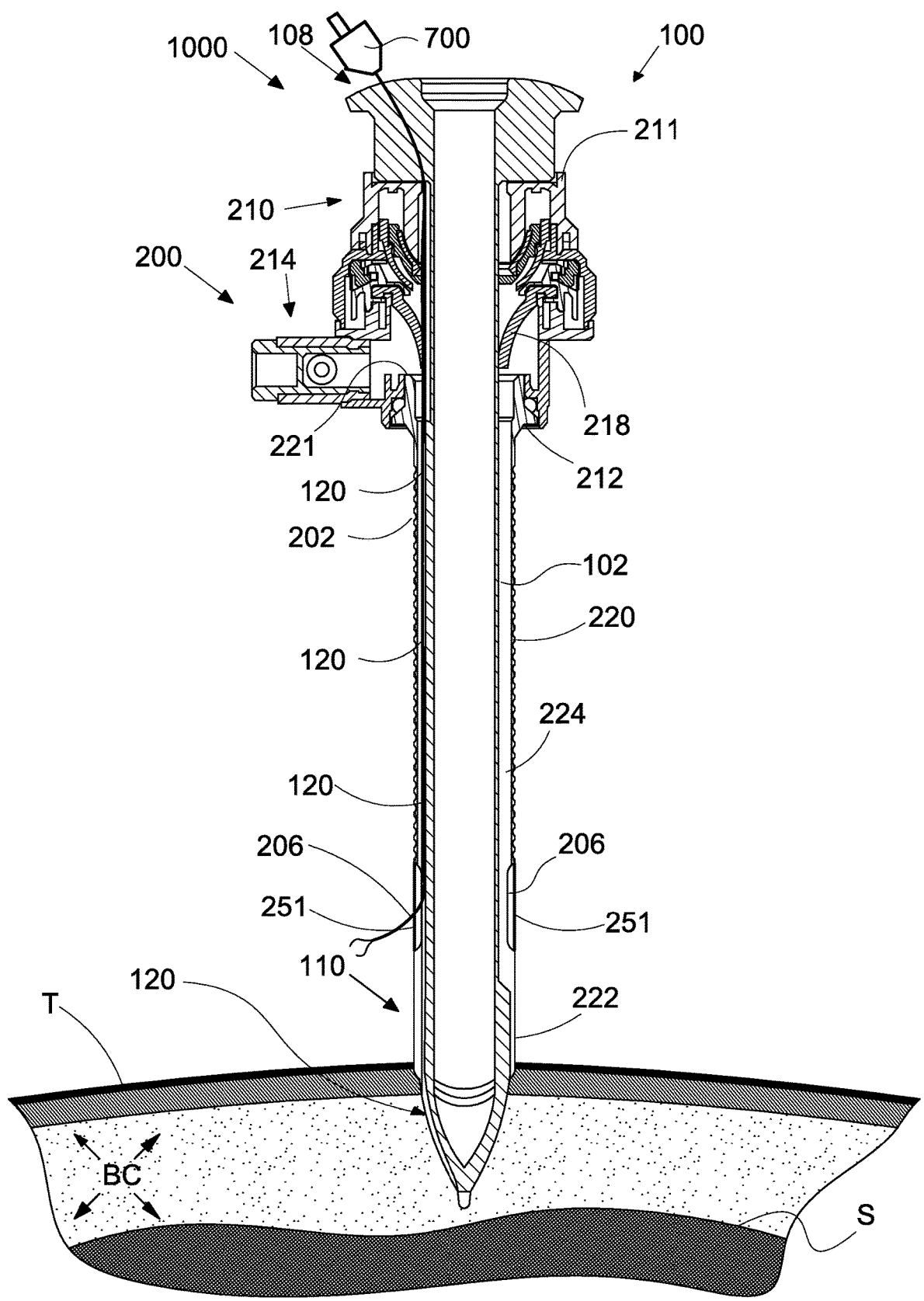
FIG. 9 is a cross-sectional view depicting a surgical instrument inserted through the channel of the obturator.
Figure 10:
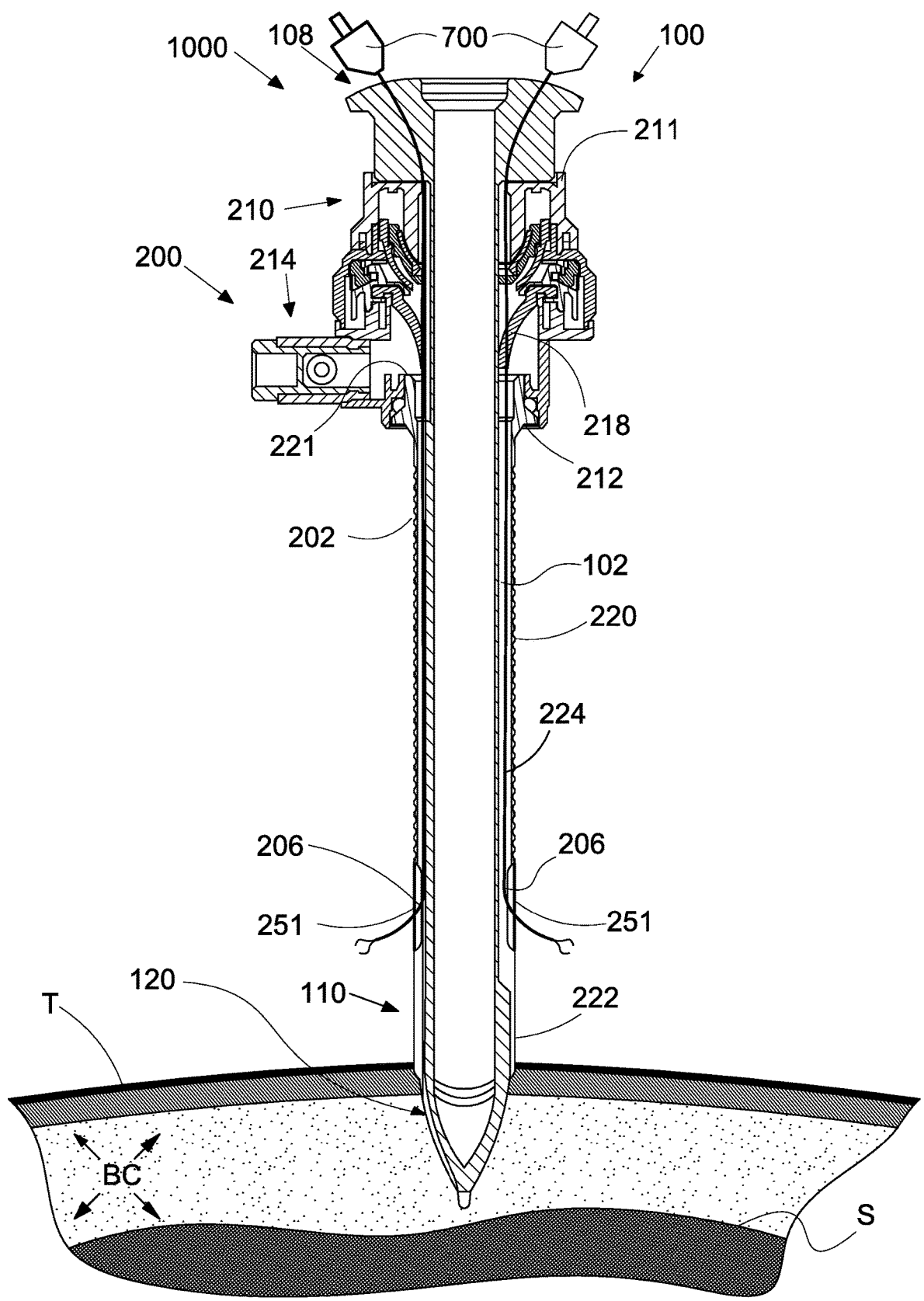
FIG. 10 is a cross-sectional view depicting two surgical instrument inserted through the obturator, with one surgical instrument inserted through the channel of the obturator.

The introduction of pressurized insufflation fluids F into body cavity BC creates an insufflated workspace such that tissue T may be lifted away from underlying structures S (see FIGS. 9 and 10). The positioning of the channel 120 across the length of the outer surface of the obturator 100 enables insufflation fluids to begin to be introduced into the body cavity BC almost immediately upon the distal tip 112 of the tip member 110 penetrating through the abdominal wall and under observation by a surgeon when an endoscope is positioned within the obturator shaft 102. Accordingly, a larger working space is created for a minimally invasive procedure such that further advancement of the obturator 100 safely into body cavity BC is possible, facilitating, e.g., further visualization or illumination of the body cavity BC, or further dilation of tissue T or structures S to reach a desired working site. Once the tissue, e.g., the abdominal wall, has been fully penetrated, the obturator 100 may be withdrawn from the cannula 200, and another instrument (not shown) may be inserted through the cannula 200. As described above, the seal member 218 may be configured to maintain insufflation fluids F within body cavity BC in the absence of obturator 100 or another instrument.

Regarding FIG. 9, a cross-sectional view depicting a surgical instrument 700 inserted through the channel 120 of the obturator 100 is shown. The surgical instrument 700 is inserted through the obturator 100 such that the distal end of the surgical instrument 700 is directed or guided through the channel 120. The distal end of the surgical instrument 700 exits the corresponding slot 206 of cannula 200 (penetrating the sealing member 251 disposed thereabout), tissue, and into the internal surgical site. Therefore, the channel 120 is configured to receive a surgical instrument 700 therethrough, a distal end of the surgical instrument configured to extend through the corresponding slot 206 of the cannula 200. In addition, as mentioned above, the channel 120 is configured to direct the insufflation fluid F toward the distal tip 112 of the tip member 110. Thus, channel 120 formed on the outer or external surface of the obturator shaft 102 and the tip member 110 serves a dual purpose. One purpose is for directing insufflation fluid F into the body cavity BC and a second purpose is for directing a surgical instrument 700 (e.g., a suture passer/grasper) to close the trocar puncture wound at the conclusion of the surgical procedure.

Moreover, elongated tubular member 202a may further include a sealing feature 251, sealingly disposed about each of slots 206 and configured to maintain a fluid-tight seal about elongated tubular member 202a to inhibit fluid exchange between longitudinal passageway 205 and the exterior of elongated tubular member 202a via slots 206. As can be appreciated, such a configuration allows for the maintenance of an insufflated internal surgical site during the course of a surgical procedure. Once maintaining insufflation is no longer necessary and/or where access through slots 206 is needed, e.g., after the surgical procedure has been completed, the sealing members 251 may be penetrated to facilitate usage of the surgical instrument 700 (see FIGS. 9 and 10).

Sealing member 251 may be formed from any suitable flexible, penetrable material, e.g., rubber, PVC, etc., and may be disposed about elongated tubular member 202a via heat shrink wrapping, overmolding, or any other suitable process. Sealing member 251 substantially conforms to the exterior configuration of elongated tubular member 202a so as to maintain the ribbed configuration of the exterior of elongated tubular member 202a.

Regarding FIG. 10, a cross-sectional view depicting two surgical instruments 700 inserted through the obturator 100 is presented, with one surgical instrument 700 inserted through the channel 120 of the obturator 100.

In FIG. 10, a first surgical instrument 700 is inserted through the obturator 100 to pass through the channel 120, such that the distal end of the surgical instrument exits the corresponding slot 206, whereas a second surgical instrument 700 is inserted through the obturator 200 to pass through the lumen 224 of the cannula shaft 220 and exit through the corresponding slot 206. Therefore, more than one surgical instrument 700 may be inserted through the obturator 100 in order for each surgical instrument 700 to engage a corresponding slot 206 of cannula 200. Therefore, the channel 120 serves the dual purpose of introducing insufflation fluids to a surgical site, as well as subsequently introducing at least one surgical instrument to the surgical site. It should be noted that, in various embodiments, the obturator shaft 102 may have a channel 120 formed on both sides thereof (such that opposing slots of the cannula can be employed simultaneously or sequentially without moving the obturator relative to the cannula), or else on only a single side thereof (whereby opposing slots of the cannula can be employed sequentially by an operator by first aligning the channel with a first slot and then subsequently rotating the obturator relative to the cannula until the channel aligns with the second slot).

The present disclosure may provide various advantages over conventional arrangements, such as obviating the use of a veress needle to introduce insufflation fluids. As shown in FIGS. 7-10, the positioning of the distal end 124 of the channel 120 across the outer surface of the obturator shaft 102 and the tip member 110 enables insufflation fluids to begin to be introduced into the body cavity BC almost immediately upon the distal tip 112 of the tip member 110 penetrating through the abdominal wall. By eliminating the use of a veress needle, this arrangement minimizes the likelihood that an injury to underlying anatomical structures will occur. The introduction of pressurized insufflation fluids F into body cavity BC in order to create an insufflated workspace (which is typically a requirement of laparoscopic surgeries such that tissue T may be lifted away from underlying structures S) is performed much more safely than with a conventional veress needle.

Still further, the present disclosure may provide various advantages over conventional arrangements such as certain optical obturators. For example, there exist optical obturators that receive endoscopes therein; these optical obturators may include holes along their shafts or at their proximal ends for allowing insufflation fluid to enter the hollow interior of the optical obturator, as well as holes near the distal end thereof for expelling the insufflation fluids from the hollow interior and into a body cavity. While these distally located holes may provide for the flow of insufflation fluids, they are located more proximally relative to its respective distalmost tip than may be achieved by the positioning of the distal end 124 of the channel 120, and thus the distalmost tip of these conventional optical obturators must be inserted farther into a body cavity in order for insufflation fluids to begin to flow into the body cavity. By needing to be inserted farther into a body cavity prior to insufflation fluids beginning to flow into the body cavity, these conventional optical obturators have a higher risk of inadvertently damaging the underlying anatomical structures.

In contrast, the distal end 124 of the channel 120 may be positioned at the distalmost end of the tip member 110. This arrangement enables insufflation fluids to begin to be introduced into the body cavity BC almost immediately upon the distal tip 112 of the tip member 110 penetrating through the abdominal wall, and earlier than would be possible in such above-described conventional optical obturators. This further reduces the likelihood that an injury to underlying anatomical structures will occur and further improves patient safety. Still another advantage of various embodiments of the present invention is that, because an outer surface of the obturator shaft and the tip member defines a channel for receiving and directing insufflation fluid into a body cavity AND a portion of the same channel is also configured to guide a surgical instrument, such as a suture passer/grasper for closing an incision, towards and through the slot, the cannula and obturator can be employed both for forming an incision at the beginning of a surgical procedure and for closing the same incision at the conclusion of the surgical procedure. Typical fascial closure devices require completely different components, or at least a fascial closure mandrel that is a separate component from the obturator. The present invention, according to various embodiments thereof, avoids this duplication of components and combines the functionality of conventional cannula/obturators and conventional fascial closure devices into a single cannula/obturator device that can perform all such functions.

A still further advantage of the present disclosure as compared to the above-described conventional optical obturators is that the provision of a channel on the outer surface of the obturator shaft and the tip member may help avoid the need for other seals that are employed in the above-described conventional optical obturators. For example, these conventional optical obturators may also include a seal at the distal end of the cannula tube, this distal cannula seal sealing between the cannula tube and the outer surface of the obturator. Such a seal is typically necessary such that insufflation fluid received via the cannula housing is directed first through the holes in the optical obturator and into the interior of the optical obturator and then out of the interior through the distalmost hole of the obturator. Without the distal cannula seal, insufflation fluid received via the cannula housing would attempt to be expelled out of the distal end of the cannula tube, between the inner wall of the cannula tube and the outer surface of the obturator, but would be prevented from doing so because of the direct contact between the tip of the optical member and the tissue. Again, this distal cannula seal adds costs and complexity to the manufacture of this conventional optical obturator, as well as provides another potential leak path during a surgical procedure.

The present disclosure, according to various embodiments thereof, may also provide the advantage that it requires virtually no modifications of the various components of a trocar. As set forth above, not only must the above-described conventional optical obturators provide two additional seals (a first seal between the interior surface of the optical obturator and the endoscope; and a distal cannula seal between the interior surface of the cannula tube and the outer surface of the optical obturator), but almost all of the components of this system are required to be re-designed as compared to an ordinary trocar in order to accommodate these seals and the desired flow of insufflation fluid into the interior of the optical obturator. In contrast, every component of the system of the present disclosure may remain completely unchanged from an ordinary trocar, thereby saving costs and enabling the advantages of the present disclosure to be provided simply by providing a channeled tip member on an ordinary trocar system, without requiring modification of the remaining components of the trocar system.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method of performing a surgical procedure comprising:
    inserting an obturator assembly into a cannula assembly having a cannula shaft defining a slot, the obturator assembly including an obturator shaft having a tip member at a distal end thereof, the obturator shaft and tip member having outer surfaces defining a channel;
    forming an incision through tissue;
    inserting the cannula assembly through the incision;
    supplying insufflation fluid along the outer surfaces of the obturator shaft and the tip member via the channel and into a body cavity; and
    inserting a surgical instrument through the channel.

2. The method according to claim 1, wherein inserting the surgical instrument includes advancing the surgical instrument through the slot of the cannula shaft.

3. The method according to claim 1, wherein inserting the surgical instrument includes the channel configured to guide the surgical instrument towards the slot.

4. The method according to claim 1, further comprising inserting an endoscope into the obturator assembly.

5. The method according to claim 1, further comprising inserting the obturator tip through tissue to create a path for the cannula.

6. The method according to claim 1, wherein inserting the obturator assembly into the cannula assembly includes the channel of the obturator shaft having a proximal-most end disposed adjacent an insufflation portion of the cannula assembly.

7. The method according to claim 1, wherein inserting the obturator assembly into the cannula assembly includes the cannula assembly being transparent.

8. The method according to claim 1, wherein inserting the obturator assembly into the cannula assembly includes inserting the obturator assembly through a lumen defined in the cannula assembly, the lumen in communication with the slot.

9. The method according to claim 8, wherein inserting the obturator assembly includes the slot having a sealing member pierceable by a distal end of a surgical instrument.

10. A method of performing a surgical procedure comprising:
    providing access through a surgical incision via a cannula assembly, the cannula assembly including a seal member and a cannula shaft defining a slot therethrough; and
    inserting an obturator assembly into the cannula assembly, the obturator assembly having an outer surface defining an uninterrupted channel configured to convey insufflation fluid from a proximal-most end of the obturator assembly to a distal-most end of the obturator assembly;
    supplying insufflation fluid into a body cavity through the uninterrupted channel; and
    inserting a surgical instrument through the uninterrupted channel.

11. The method according to claim 10, further comprising forming a seal between the cannula assembly and the obturator assembly inserted through the cannula assembly.

12. The method according to claim 10, further comprising suturing the surgical incision using a surgical instrument inserted through the slot.

13. The method according to claim 10, wherein inserting the surgical instrument includes advancing the surgical instrument through the slot of the cannula shaft.

14. The method according to claim 10, wherein inserting the obturator assembly into the cannula assembly includes the uninterrupted channel configured to guide the surgical instrument towards the slot.

15. The method according to claim 10, wherein inserting the obturator assembly into the cannula assembly includes the uninterrupted channel of the obturator assembly having a proximal-most end disposed adjacent an insufflation port of the cannula assembly.

16. The method according to claim 10, wherein inserting the obturator assembly into the cannula assembly includes inserting the obturator assembly through a lumen defined in the cannula assembly, the lumen in communication with the slot.

17. The method according to claim 16, wherein inserting the obturator assembly includes the slot having a sealing member pierceable by a distal end of a surgical instrument.

\* \* \* \* \*